US012055492B2

(12) United States Patent
Dehkordi et al.

(10) Patent No.: US 12,055,492 B2
(45) Date of Patent: *Aug. 6, 2024

(54) TEXTILE BRIGHTNESS MEASUREMENT SYSTEM

(71) Applicant: Uster Technologies AG, Uster (CH)

(72) Inventors: Peyman H. Dehkordi, Knoxville, TN (US); Kent A. Rinehart, Knoxville, TN (US); David D. McAlister, III, Knoxville, TN (US)

(73) Assignee: Uster Technologies AG, Uster (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/496,340

(22) Filed: Oct. 27, 2023

(65) Prior Publication Data
US 2024/0068945 A1 Feb. 29, 2024

Related U.S. Application Data

(63) Continuation of application No. 15/733,745, filed as application No. PCT/CH2019/000014 on May 2, 2019, now Pat. No. 11,835,459.

(Continued)

(51) Int. Cl.
G01N 21/64 (2006.01)
G01N 21/55 (2014.01)
G01N 33/36 (2006.01)

(52) U.S. Cl.
CPC ......... *G01N 21/6456* (2013.01); *G01N 21/55* (2013.01); *G01N 33/367* (2013.01);
(Continued)

(58) Field of Classification Search
CPC .. G01N 33/367; G01N 21/8983; G01N 21/93; G01N 21/8806; G01N 21/645;
(Continued)

(56) References Cited

U.S. PATENT DOCUMENTS 8,199,319 B2 * 6/2012 Baxter .................. G01N 21/94
356/402
9,958,265 B2 * 5/2018 Nagai ................. G01N 21/8422
(Continued)

FOREIGN PATENT DOCUMENTS

| CN | 101584572 A | 11/2009 |
| EP | 0293810 B1 | 4/1991 |
| WO | 2013017738 A1 | 2/2013 |

*Primary Examiner* — An H Do
(74) *Attorney, Agent, or Firm* — TechnicalAttorney; Rick Barnes

(57) ABSTRACT

An apparatus for measuring not only the reflected radiation but also the fluorescence emission of a textile sample, which includes a presentation subsystem having a viewing window. A radiation subsystem has a tunable radiation source for directing a desired radiation having a wavelength range and an intensity through the viewing window toward the sample, and thereby causing the sample to produce a fluorescence. A sensing subsystem has an imager for capturing the reflected radiation and fluorescence in an array of pixels. A control subsystem has a processor, for controlling the presentation subsystem, the radiation subsystem, and the sensing subsystem, and creates a reflected radiation and fluorescence image containing both spectral information and spatial information in regard to the reflected radiation and fluorescence #843 of the sample.

21 Claims, 9 Drawing Sheets

Related U.S. Application Data

(60) Provisional application No. 62/666,125, filed on May 3, 2018.

(52) U.S. Cl.
CPC ............... $G01N\ 2021/6471$ (2013.01); $G01N\ 2201/062$ (2013.01); $G01N\ 2201/127$ (2013.01)

(58) Field of Classification Search
CPC ............ G01N 21/55; G01N 21/6456; G01N 2021/8845; G01N 2021/6471; G01N 2201/062; G01N 2201/127; G10L 17/18
See application file for complete search history.

(56) References Cited

U.S. PATENT DOCUMENTS

| | | | |
|---|---|---|---|
| 10,365,210 B2 * | 7/2019 | Chenault | G06V 10/145 |
| 11,835,459 B2 * | 12/2023 | Dehkordi | G01N 21/6456 |
| 2006/0132777 A1 | 6/2006 | Hubble, III et al. | |
| 2008/0144013 A1 | 6/2008 | Lanoue et al. | |
| 2013/0155402 A1 | 6/2013 | Walton et al. | |
| 2015/0131090 A1 | 5/2015 | Osumi | |
| 2016/0116410 A1 | 4/2016 | Blasinski et al. | |
| 2016/0258881 A1 | 9/2016 | Bown et al. | |
| 2019/0195689 A1 | 6/2019 | Mcquilkin et al. | |
| 2022/0276168 A1 | 2/2022 | Dehkordi | |

* cited by examiner

TEXTILE BRIGHTNESS MEASUREMENT SYSTEM

FIELD

This invention relates to the field of textile characteristics measurement. More particularly, this invention relates to the measurement of the brightness (fluorescence and reflected light) characteristics of textiles for online and offline applications.

INTRODUCTION

Textiles are woven or knitted fabrics made from yarn, but they also include fibers (natural, manmade, and blend), yarn, or any other product made from these combinations. The visual perception of the final fabric is very important to the end user. Visual perception includes, but is not limited to, pattern, color, and brightness. Brightness is commonly defined as an attribute of visual perception in which a source appears to be radiating or reflecting light. For textile, the brightness is a function of reflected light and fluorescence emission. Fluorescent pigments are one method of adding brightness to the fabric. A fluorescent material is defined as a material that emits optical radiation after having absorbed light or other electromagnetic radiation, typically at wavelengths that are longer than the wavelengths of the electromagnetic radiation absorbed. Therefore, fluorescent material not only reflects the incident light but also emits an additional light at longer wavelengths. Especially if the absorbed electromagnetic radiation is in the ultraviolet (UV) range and the emitted light is visible, the fluorescent material appears to be brighter.

There are at least three major categories of fluorescent pigments: inorganic fluors, optical whiteners, and daylight fluorescents. Their major differences are in their chemical composition and optical characteristics, and thus their application. For example, inorganic fluors are usually activated by optical radiations in the range of ultraviolet (UV) to visible (300-420 nm) light, whereas optical whiteners are activated in the range of near UV (340-400 nm), and daylight fluorescents are activated and emit in the visible range (400-700 nm).

Fluorescent properties can be given to textiles in a variety of ways, such as, but not limited to (a) coating fabrics with fluorescent material in a resin mix, (b) introducing fluorescent material to the fibers at the spinning stage, (c) coating the fibers, and (d) textile finishing or domestic laundering with fluorescent material.

The quality and application of the fluorescent pigments are important parameters to maintain, monitor, and control for best cosmetic performance in the textile process. While these methods have been around for many years, the formulation and quality control of the fluorescent material application have been challenging, primarily due to lack of proper measurement instrumentation and lack of understanding of the fluorescent material.

What is needed, therefore, is a system for measuring not only the reflected radiation but also the fluorescence emissions (altogether the brightness) that tends to reduce issues such as those described above, at least in part.

SUMMARY

The above and other needs are met by an apparatus for measuring reflected radiation and fluorescence of a textile sample, including a presentation subsystem having a viewing window, and a radiation subsystem having a tunable radiation source adapted to direct a desired radiation having a wavelength range and an intensity through the viewing window toward the sample, and cause the sample to produce a fluorescence. A sensing subsystem has an imager adapted to capture the reflected radiation and fluorescence in an array of pixels, where each pixel records an intensity of the fluorescence at the pixel location. A control subsystem includes a processor adapted to control the presentation subsystem, the radiation subsystem, and the sensing subsystem, and to create a reflected radiation and fluorescence image containing both spectral information and spatial information in regard to the reflected radiation and fluorescence of the sample. The control subsystem is configured to perform a pattern analysis with the reflected radiation and fluorescence image, which pattern analysis includes at least one of, (a) a number of patterns found in the brightness image, (b) a total area of all patterns in the brightness image, (c) an average size of all patterns, (d) a percentage of patterns with a horizontal orientation, (e) a percentage of patterns with a vertical orientation, or (f) a percentage of patterns with a nonordinal orientation.

In various embodiments according to this aspect of the disclosure, the presentation subsystem further includes a sample press adapted to press the sample against the viewing window. In some embodiments, the presentation subsystem further includes calibration tiles adapted to produce reflected radiation and fluorescence with known characteristics in response to radiation having known characteristics. In some embodiments, the radiation subsystem further includes optics adapted to shape and filter the radiation from the tunable radiation source before the radiation achieves the sample. In some embodiments, the radiation subsystem further includes a detector adapted to detect characteristics of the radiation. In some embodiments, the tunable radiation source further includes a source capable of producing two or more discrete radiation ranges. In some embodiments, the tunable radiation source further includes a radiation source capable of producing the radiation at a desired intensity.

In some embodiments, the radiation source further includes a source capable of producing two or more discrete radiation ranges, and further capable of independently producing each of the two or more radiation ranges at different desired intensities. In some embodiments, the sensing subsystem further includes an imager adapted to capture the reflected radiation and fluorescence in a two-dimensional array of pixels. In some embodiments, the sensing subsystem further includes a variable filter adapted to selectively prohibit portions of the fluorescence from achieving the imager. In some embodiments, the control subsystem further includes a machine interface adapted to receive commands from and send information to another instrument.

In some embodiments, the control subsystem further includes a human interface adapted to receive commands from and send information to a user. In some embodiments, the control subsystem is configured to classify patterns in the reflected radiation and fluorescence image, including a percentage of the reflected radiation and fluorescence image individually represented by each one of the patterns. In some embodiments, the control subsystem is configured to classify patterns in the reflected radiation and fluorescence image, including an orientation of each one of the patterns, where the orientation is at least one of horizontal, vertical, and non-ordinal.

According to another aspect of the present disclosure, there is described a method for measuring fluorescence of a textile sample by presenting the sample against a viewing window with a presentation subsystem, and directing a desired radiation having a wavelength range and an intensity from a radiation source through the viewing window toward the sample, thereby causing the sample to produce a fluorescence. The reflected radiation and fluorescence are captured with a sensing subsystem, which includes an imager in an array of pixels, where each pixel records an intensity of the reflected radiation and fluorescence at the pixel location. A processor controls the presentation subsystem, the radiation subsystem, and the sensing subsystem. A reflected radiation and fluorescence image are created, containing both spectral information and spatial information in regard to the reflected radiation and fluorescence of the sample. The processor performs a pattern analysis with the fluorescent and reflected radiation image, which pattern analysis includes at least one of, (a) a number of patterns found in the brightness image, (b) a total area of all patterns in the brightness image, (c) a average size of all patterns, (d) a percentage of patterns with a horizontal orientation, (e) a percentage of patterns with a vertical orientation, or (f) a percentage of patterns with a nonordinal orientation.

Various embodiments according to this aspect of the disclosure include pressing the sample against the viewing window with a press. Some embodiments include shaping and filtering the radiation from the radiation source with optics before the radiation achieves the sample. Some embodiments include detecting characteristics of the radiation with a detector. Some embodiments include producing two or more discrete radiation ranges at desired intensities. Some embodiments include selectively prohibiting portions of the reflected radiation and fluorescence from achieving the imager. Some embodiments include classifying patterns in the reflected radiation and fluorescence image, including a percentage of the reflected radiation and fluorescence image individually represented by each one of the patterns.

DRAWINGS

Further advantages of the invention are apparent by reference to the detailed description when considered in conjunction with the figures, which are not to scale so as to more clearly show the details, wherein like reference numbers indicate like elements throughout the several views, and wherein.

DESCRIPTION

Figure 1:
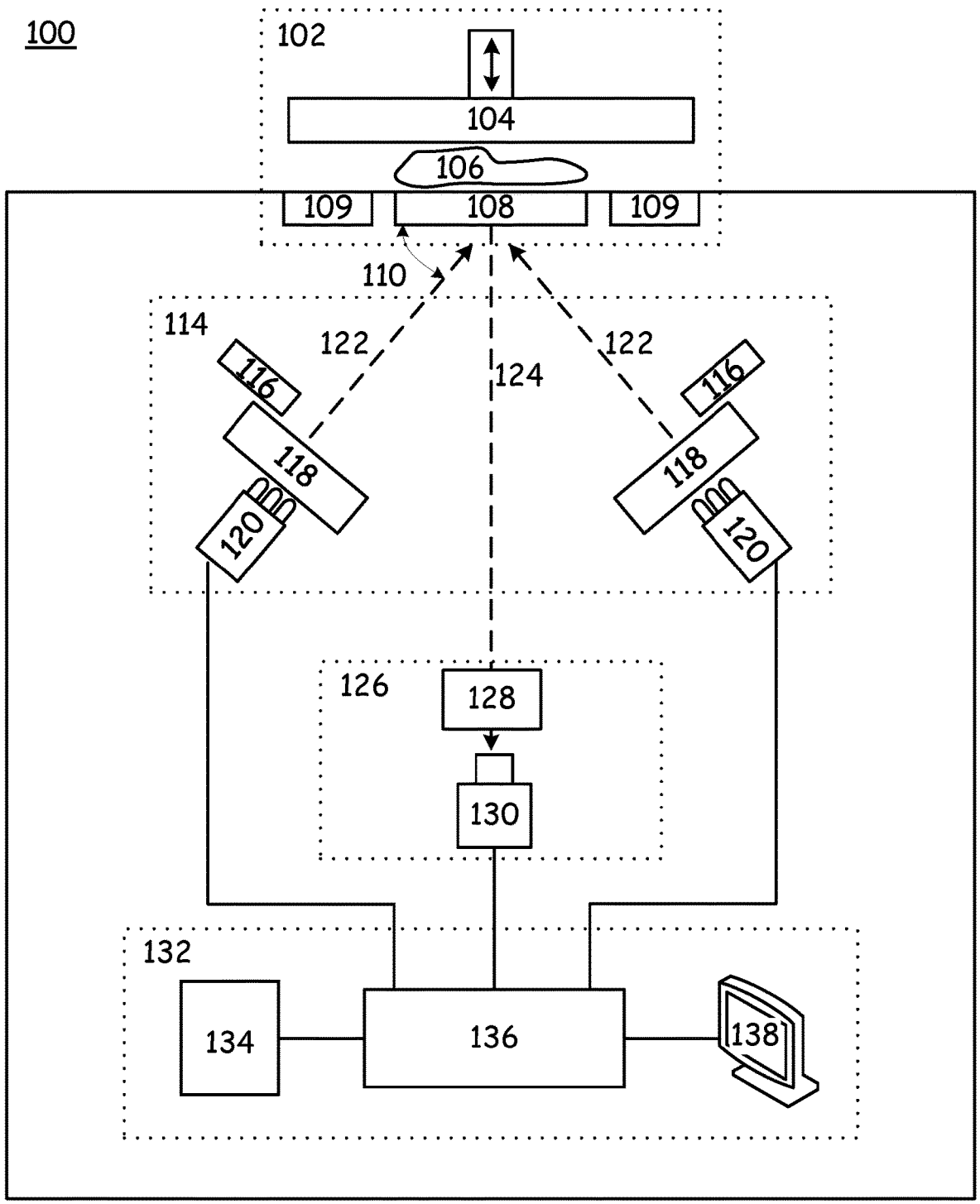
FIG. 1 is a functional block diagram of a measurement device, according to an embodiment of the present invention.

With reference now to FIG. 1, there is depicted a reflected radiation and fluorescence (altogether brightness) measurement system 100, which can be used for both offline and online measurements. The system 100 includes a sample presentation subsystem 102, a radiation subsystem 114, a sensing subsystem 126, and a control subsystem 132, each as explained in more detail below.

FIG. 1 also shows additional aspects of the reflected radiation and fluorescence measurement system 100, which include a sample material 106 to be measured, a sample press 104, a sample window 108, reference fluorescent tiles 109, radiation sources 120, radiation shaping and filtering optics 118, radiation measurement radiometers 116, a variable optical filter 128, an imager 130, a signal processor 136, a user interface 138, and a machine interface 134, all of which are described in more detail within their relevant subsystems, below.

Sample Presentation Subsystem

The sample presentation subsystem 102 presents the sample fluorescent material 106 to the measurement system 100. The sample 106 may be any form of textile including, but not limited to, fibers, slivers, or fabrics. Some embodiments include two presentation goals. One is to present as much of the sample 106 to the measurement system 100 as reasonable, and the other is to present a consistent sample angle. One method to realize these goals is by using a sample press 104 that presses the sample 106 to the sample window 108 using a consistent pressure.

The sample presentation subsystem 102 also includes reference fluorescent tiles 109, whose reflected radiation and fluorescent characteristics are known. The intent of the reference fluorescent tiles 109 is to allow the measurement system 100 to self-calibrate to a known reference reflected radiation and fluorescence level. Furthermore, it serves as a self-test where the measurement system 100 can automatically detect malfunctioning situations due to a component failure, and so forth. When the system 100 is measuring a sample 106, the reference fluorescent tiles 109 can either be shielded from the radiation 122 so that they do not reflect/fluoresce, or the reflection/fluorescence that they produce can be shielded from the imager 130 in some manner, so that they do not confound the fluorescence readings from the sample 106.

Radiation Subsystem

The radiation subsystem 114 is responsible for radiating and exciting the fluorescent sample 106 with radiation 122 having a desired profile in terms of constituent wavelengths and their associated energies. Specifically, the intent is to control and ensure a known radiation 122 profile on the sample 106. The desired radiation 122 profile is dependent, at least in part, on the characteristics of sample 106 and the properties of the sample 106 to be measured. The desired radiation 122 profile is controlled as described hereinafter. Some parameters of the radiation 122 include, but are not limited to, wavelength, power, beam uniformity, and beam angle 110, which is the angle between the radiation sources 120 and the plane of the sample window 108. For example, in one embodiment, when the sample 106 contains an optical whitener material, the radiation sources 120 operate in the near ultraviolet range (340-400 nm) and the beam angle 110 is set at forty-five degrees, as shown in FIG. 1. Yet in another embodiment, the radiation sources 120 operate in the visible range (400-700 nm) and the beam angle 110 is set at forty-five degrees, as shown in FIG. 1.

The radiation subsystem 114 may include multiple radiation sources 120 arranged in different configurations. For example, in one embodiment, the configuration may incorporate two radiation sources 120 that are directed in opposite directions, as shown in FIG. 1. Whereas in another embodiment, it may incorporate four radiation sources 120, where the sample 106 is radiated from four different directions.

In some embodiments, the radiation sources 120 can be moved within the system 100. For example, in some embodiments the sources 120 can be moved to provide different incident angles of the radiation 122 on the sample window 108. In some embodiments, the sources 120 can be moved so that they have a different proximity to the sample window 108, or a different radial angle.

An example of a radiation source 120 may include, but is not limited to, one or more of light emitting diodes (LED), halogen lamps, mercury vapor lamps, incandescent lamps, deuterium lamps, fluorescent lamps, and xenon lamps. Furthermore, each radiation source 120 may incorporate one or more of the afore-mentioned lamps. For example, one embodiment may include several groups of visible and ultraviolet LEDs, where each LED group operates at different wavelengths. In such an embodiment, each LED group can be controlled separately from the other groups by the processor 136.

In one embodiment, the sample 106 is irradiated with visible light, and a color measurement is made on the sample 106 in the CIELAB color space. This color image of the sample 106 is treated in the same manner as described below for all other images.

Therefore, the output levels and spectral characteristics of the radiation sources 120 can be customized for a given fluorescence application and measurement, as exemplified in FIGS. 2A-2D, wherein the graphs 200 depict the radiation 122 wavelength on the x-axis 204, and the radiation 122 output level on the y-axis 202. In these examples there are two groups of ultraviolet LEDs operating at 360 nm and 380 nm, in various combinations and at various intensities.

Figure 2A:
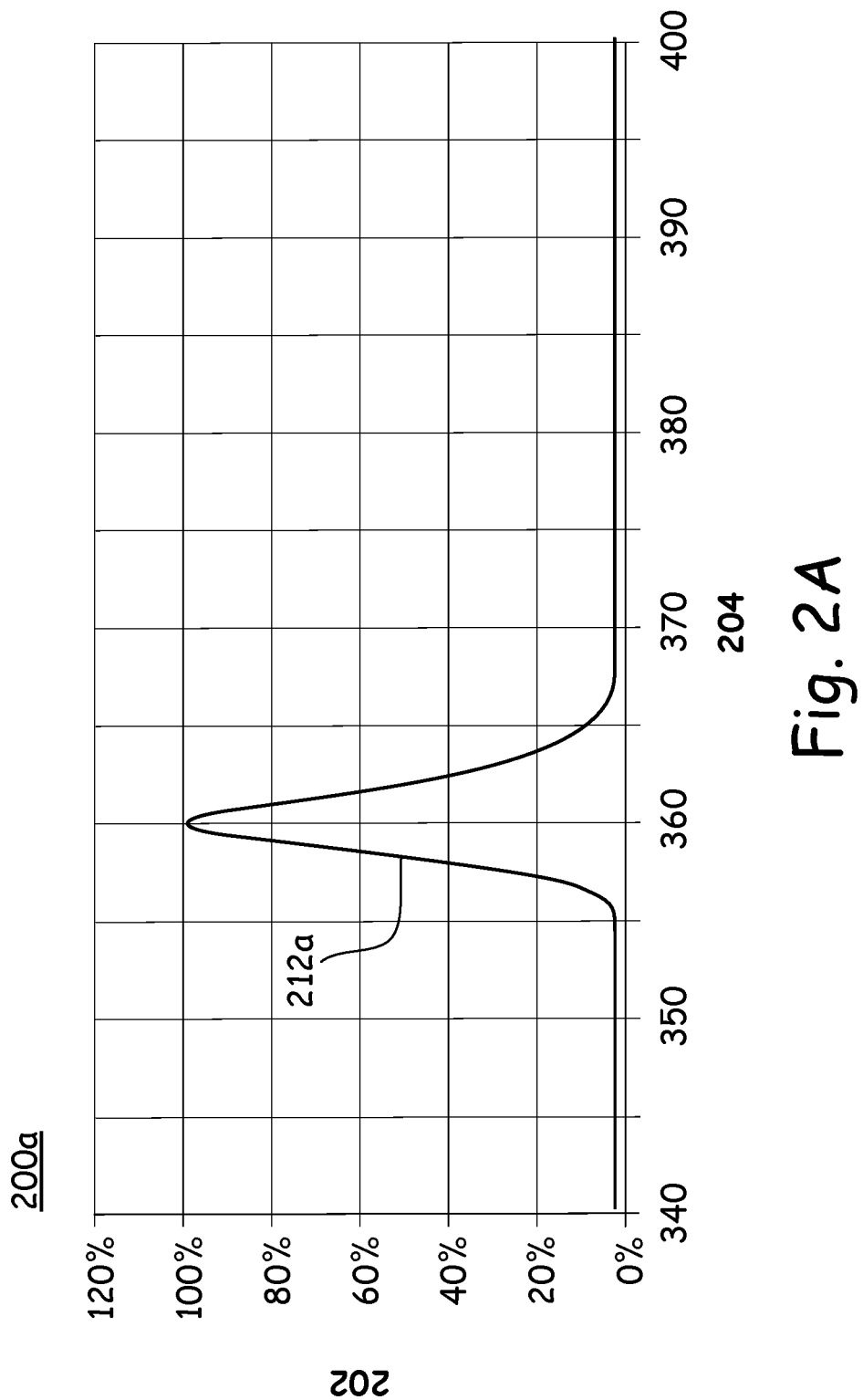
FIGS. 2A-2D are graphs of radiation source wavelength versus output level for a selection of radiation profiles, according to various embodiments of the present invention.
Figure 2B:
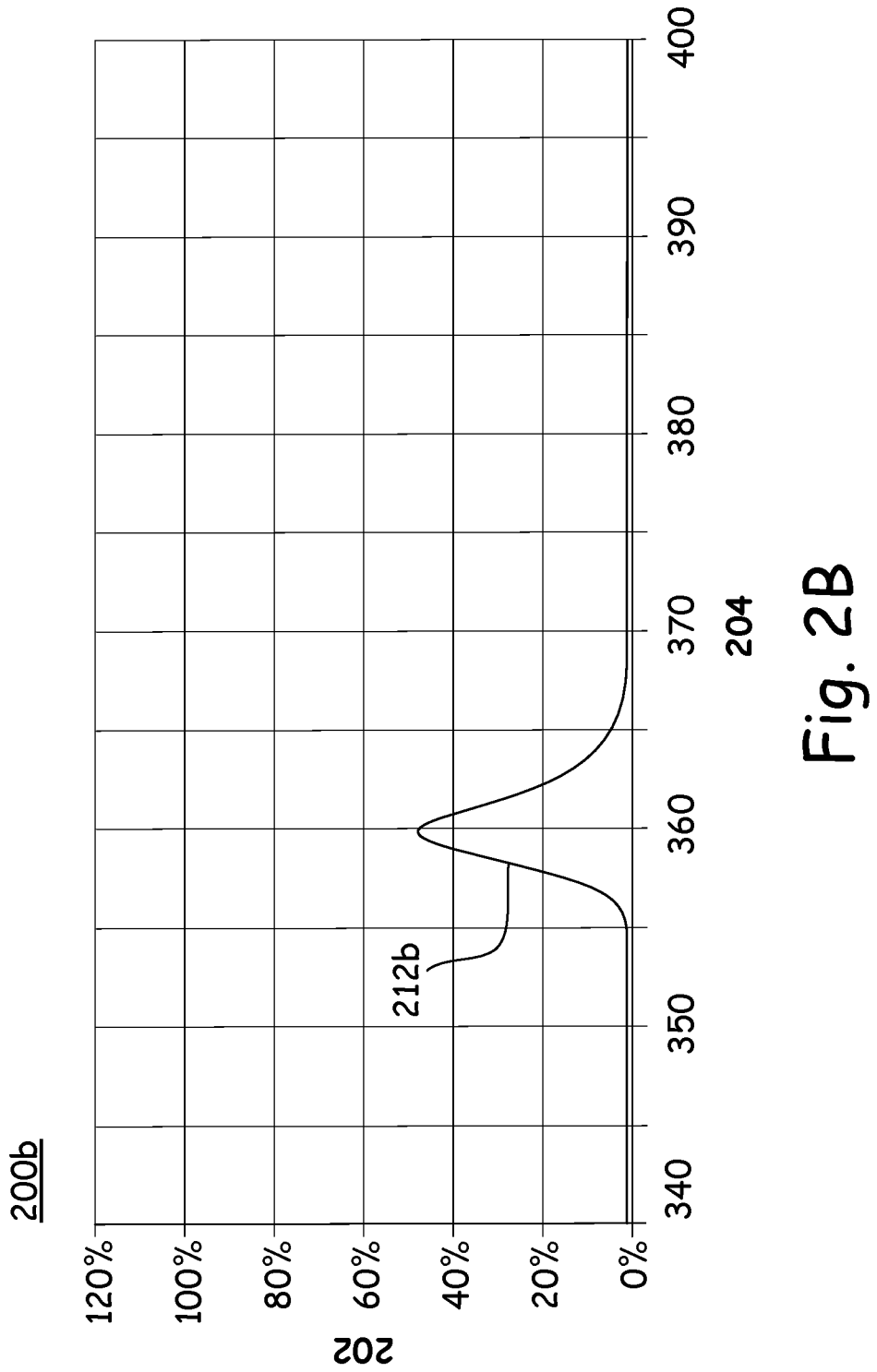
Figure 2C:
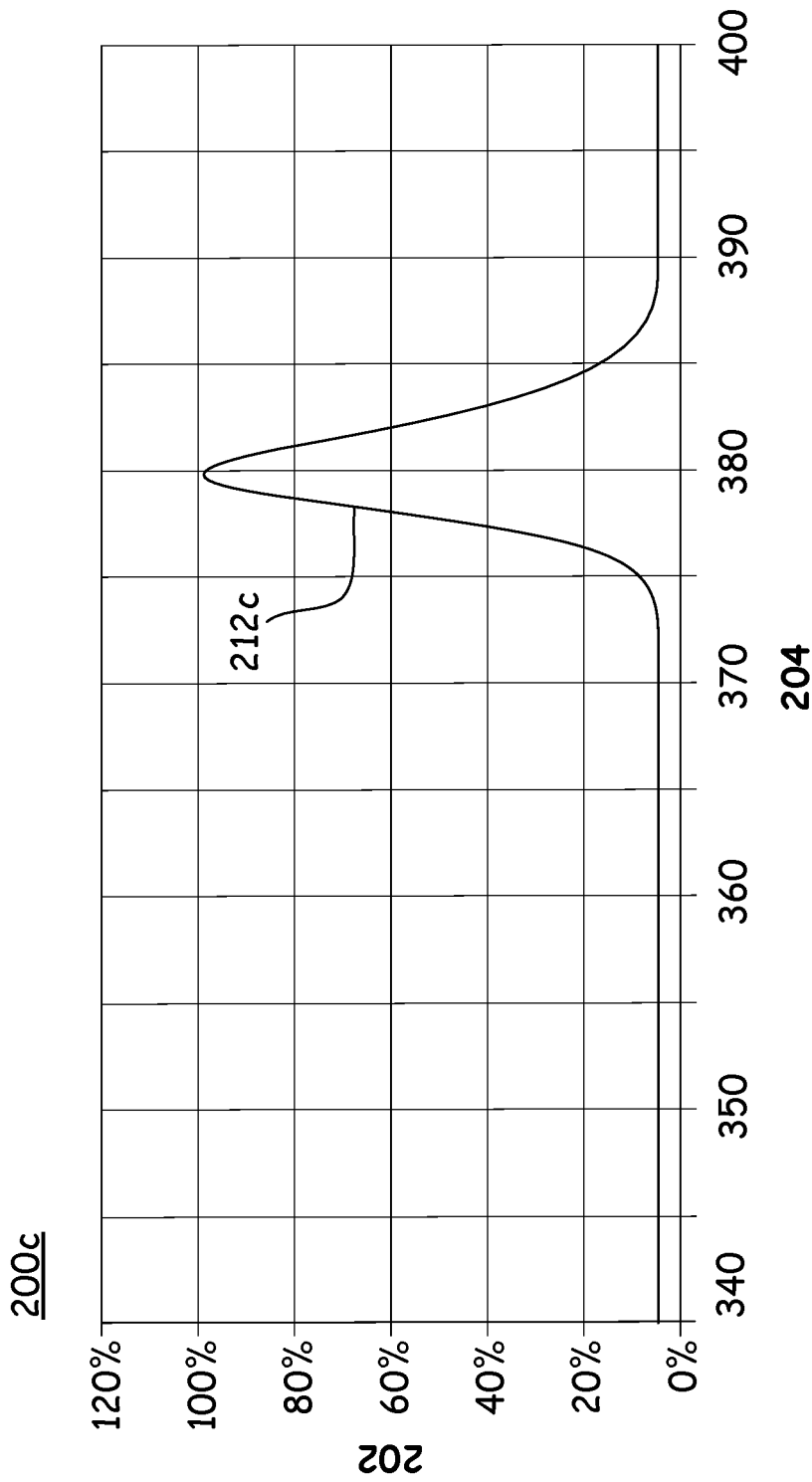
Figure 2D:
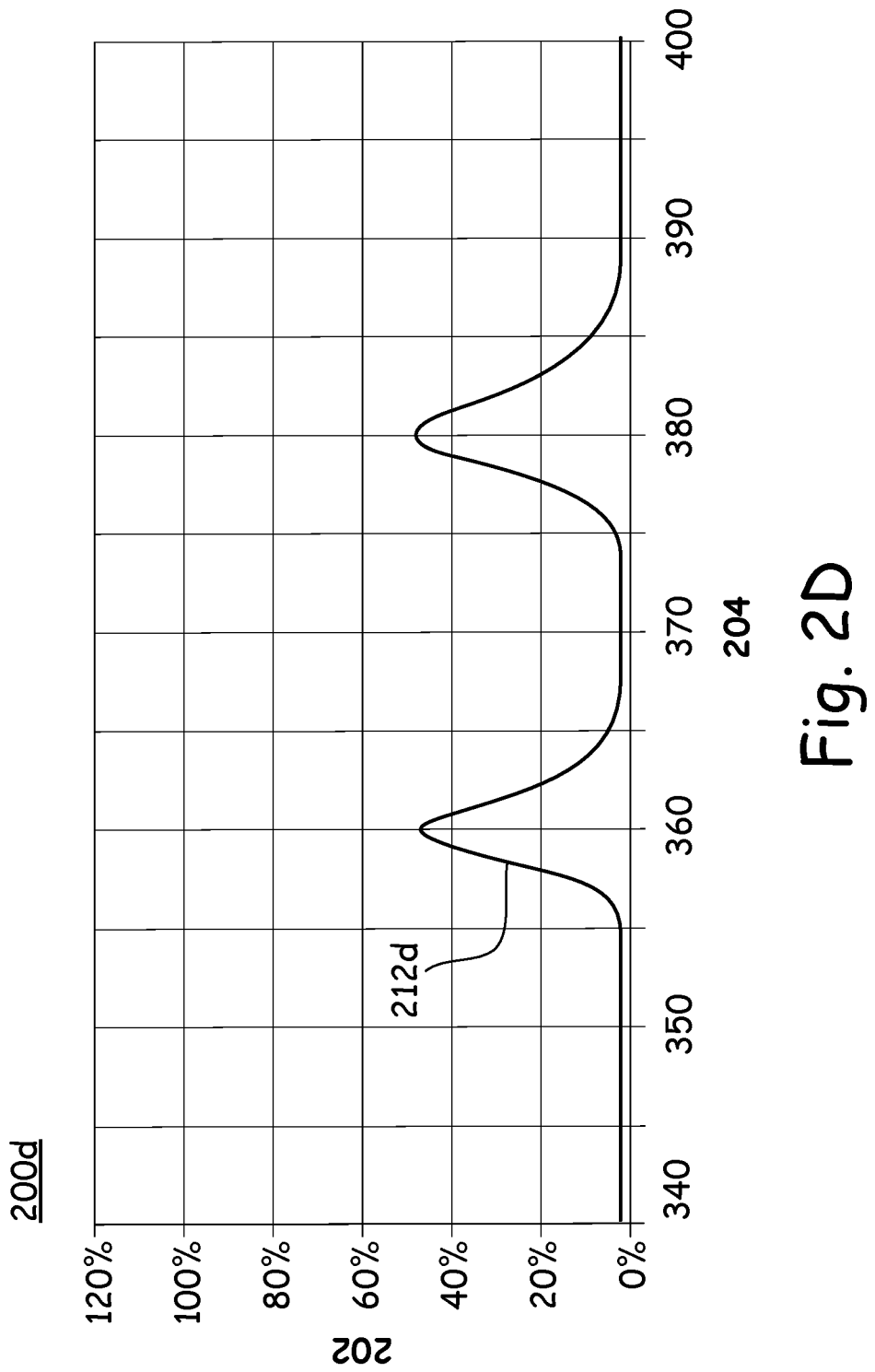

In graph 200a of FIG. 2A, the 360-nm LED group is operational at its full output level, as depicted by spectrum 212a. In graph 200b of FIG. 2B, the 360-nm LED group is operating at the 50% output level, as depicted by spectrum 212b. In both FIGS. 2A and 2B, the 380-nm LED group is completely turned off. FIG. 2C depicts an example 200c where the 380-nm LED group is operating at its full output level, but the 360-nm LED group is completely turned off. FIG. 2D shows yet another example 200d where both LED groups are running at a 50% output level. Other combinations of wavelength and output level are also contemplated herein.

One design goal is to maintain radiation 122 uniformity and stability over the area of the sample window 108 and/or over the area of the sample 106. One approach is to use radiation 122 shaping and filtering optics 118 to fine tune the radiation 122 to a desired wavelength range, and to shape the radiation 122 for uniformity, directionality, and coverage. In some embodiments, the radiation 122 is monitored and regulated through closed-loop feedback control via radiation 122 detectors 116.

Sensing Subsystem

The sensing subsystem 126 is responsible for sensing and measuring the reflected radiation and the fluorescent characteristics of the sample 106 while it is irradiated. One goal is to spectrally separate the reflected radiation 122 from the emitted fluorescent signal 124. One method to accomplish this is with a variable optical filter 128. For example, in one embodiment where the sample 106 includes an optical whitener, the radiation sources 120 are set to operate in an ultraviolet spectral range of 340-400 nm, and the fluorescent emissions 124 are in a 420-470 nm spectral range. In this case, the variable optical filter 128 rejects any spectral signals in 340-400 nm range, and only passes radiation in the 420-470 nm range. Alternately, for another application, the variable optical filter 128 rejects one range and passes another range, as indicated by the given application. One method to implement the variable optical filter 128 is to incorporate a filter-wheel with several band pass filters, where the processor 136 controls the filter-wheel and selects the appropriate band pass filter for a given application.

The actual fluorescence sensing and measuring is performed by the imager 130. The imager 130 not only measures the amount of fluorescence emissions and reflected radiation 124, but also measures the distribution and spatial characteristic of the fluorescence emissions and reflected radiation 124 within the field of view of the imager 130. In one embodiment, the imager 130 may be a focal-plane two-dimensional array device that is sensitive in the desired fluorescent emissions and reflected radiation spectral ranges. In another embodiment, the imager 130 may be a line scan array that is scanned across the field of view to create a two-dimensional image. The scanning can be accomplished either by mechanical movement of the imager 130 or via mechanical movement of a mirror onto a stationary imager 130. In yet another embodiment, the imager 130 may be a hyper-spectral imaging device. Regardless of the specific imaging method employed, the measurement for a given sample 106 includes the fluorescence level, the spectral response, and the spatial information. For the remainder of this document, we refer to this output of the imager 130 as the fluorescent image.

The online sensing can be done in either a static mode or a dynamic mode. In static mode, the sample 106 is brought into the field of view of the imager 130 on the sample window 108 and stops for the measurements. In dynamic mode, the sample 106 moves across the sample window 108, and the radiation subsystem 114 and the sensing subsystem 126 operate at a speed that is fast enough related to the speed of the sample movement. In an offline mode, the sample 106 can be placed on the sample 108 manually, as desired.

Control Subsystem

The control subsystem 132 is responsible for controlling, processing, and interfacing functions of the system 100. This is accomplished under the control of a processor 136. The control functions include, but are not limited to, controlling the operation of the other subsystems in the manner as generally described elsewhere herein. It also processes the image via the measurement method selected. The result of the measurement method is communicated to the user interface 138 and/or to a machine interface 134. The machine interface 134 may include, but is not limited to, an electronic interface to a textile machine or an information system.

Measurement Method

Figure 4:
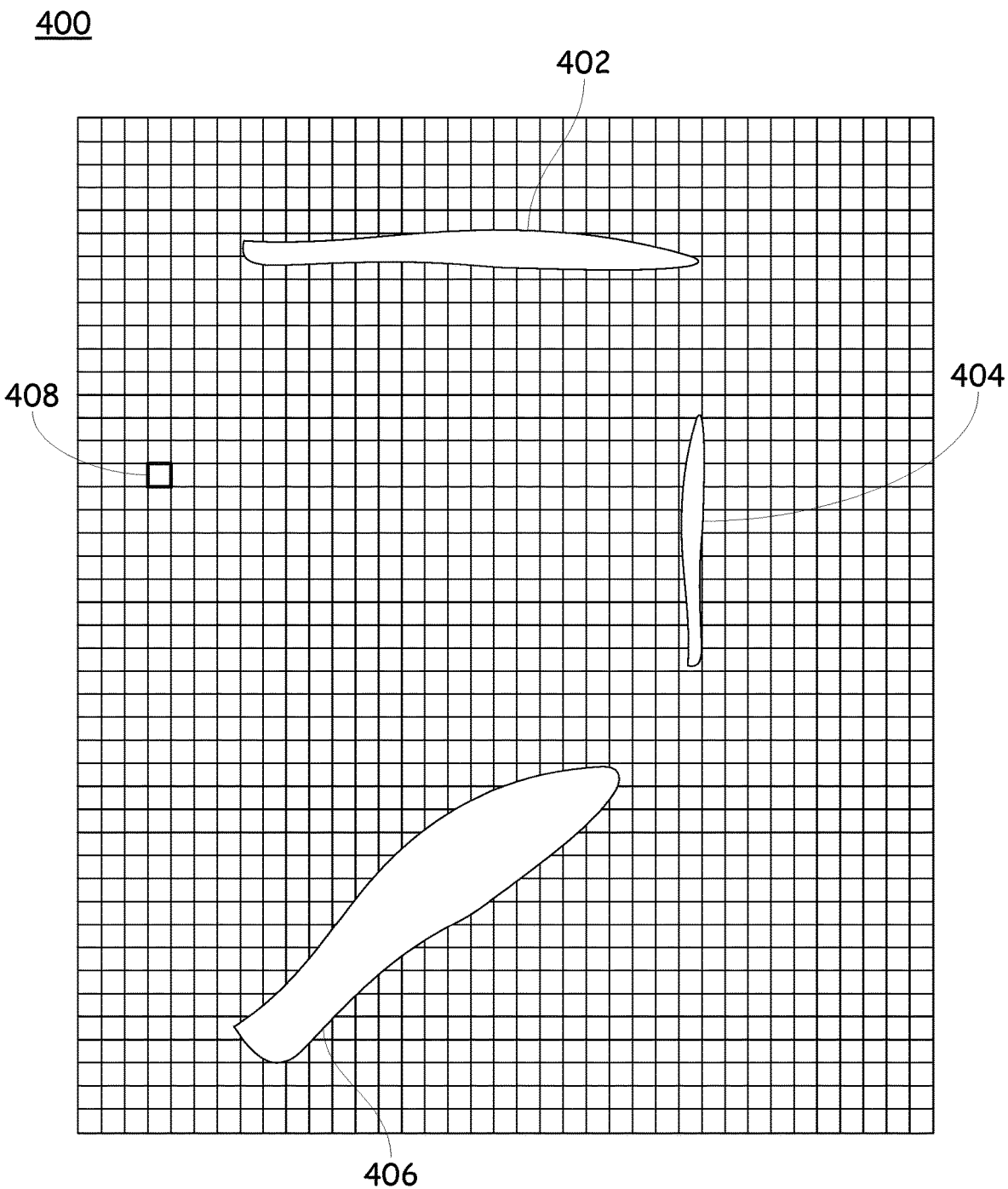
FIG. 4 is an example of a fluorescence pattern, according to an embodiment of the present invention.

The measurement method is based on processing both the reflected radiation and the fluorescent emission image, which may be a one- or two-dimensional image, where each pixel 408 (one image element, as depicted in FIG. 4) represents the brightness level of a particular location on the sample 106. The measurements may include, but are not limited to, two categories, which are (a) statistical analysis, and (b) pattern analysis.

Statistical Analysis

The first measurement category is based on the statistical analysis, which provides basic statistical assessment of the brightness level, which may include (a) average brightness level, (b) minimum brightness level and location of same, (c) maximum brightness level and location of same, (d) uniformity of the brightness level, and (e) a graph of the brightness.

Therefore, for a given brightness sample 106 that is irradiated with an appropriate radiation subsystem 114, the brightness image can be presented as:

$$BI(\lambda_j) = a(\lambda_j) * FI \begin{bmatrix} i_{11} & \cdots & i_{1n} \\ \vdots & i_{xy} & \vdots \\ i_{m1} & \cdots & i_{mn} \end{bmatrix} + b(\lambda_j) * LI \begin{bmatrix} i_{11} & \cdots & i_{1n} \\ \vdots & i_{xy} & \vdots \\ i_{m1} & \cdots & i_{mn} \end{bmatrix}, \quad (1)$$

Where:
$a(\lambda_j)$ is weighting factor for the fluorescence image of wavelengths,
where $\lambda_{min} < \lambda_j < \lambda_{max}$, =1, 2, . . . , k,
$b(\lambda_j)$ is weighting factor for the Luminance image of wavelengths,
where $\lambda_{min} < \lambda_j < \lambda_{max}$, j=1, 2, . . . , k,
$BI(\lambda_j)$ is the brightness image of the sample 106 for one or more ranges of wavelengths, where $\lambda_{min} < \lambda_j < \lambda_{max}$, j=1, 2, . . . , k,
$FI(\lambda_j)$ is the fluorescence image of the sample 106 for one or more ranges of wavelengths, where $\lambda_{min} < \lambda_j < \lambda_{max}$, j=1, 2, . . . , k,
$LI(\lambda_j)$ is the luminance image of the sample 106 for one or more ranges of wavelengths, where $\lambda_{min} < \lambda_j < \lambda_{max}$, j=1, 2, . . . , k,
n is the number of spatial points for the image in the horizontal diretion,
m is the number of spatial points for the image in the vertical diretion, and
$i_{xy}$ is the energy level of the sample at coorindate location of x and y at wavelength $\lambda_j$.

The statistical assessment of the brightness level for the sample 106 can be computed as:

$$Avg(\lambda_j) = \overline{BI(\lambda_j)} = \frac{\sum_{x=1}^{n} \sum_{y=1}^{m} i_{xy}}{m * n}, \quad (2)$$

$$Min(\lambda_j) = min(BI(\lambda_j)) = min \begin{bmatrix} i_{11} & \cdots & i_{1n} \\ \vdots & i_{xy} & \vdots \\ i_{m1} & \cdots & i_{mn} \end{bmatrix}, \quad (3)$$

$$Max(\lambda_j) = max(BI(\lambda_j)) = max \begin{bmatrix} i_{11} & \cdots & i_{1n} \\ \vdots & i_{xy} & \vdots \\ i_{m1} & \cdots & i_{mn} \end{bmatrix}, \text{ and} \quad (4)$$

$$Unif(\lambda_j) = 100 * \left(1 - \frac{std(BI(\lambda_j))}{Avg(\lambda_j)}\right), \quad (5)$$

where:
$Avg(\lambda_j)$ is the overall brightness level of the sample 106 for a single range or multiple ranges of wavelengths, where $\lambda_{min} < \lambda_j < \lambda_{max}$, j=1, 2, . . . , n,
$Min(\lambda_j)$ is the minimum brightness level of the sample 106 for a single range or multiple ranges of wavelengths, where $\lambda_{min} < \lambda_j < \lambda_{max}$, i=1, 2, . . . , n,
$Max(\lambda_j)$ is the maximum brightness level of the sample 106 for a single range or multiple ranges of wavelengths, where $\lambda_{min} < \lambda_j < \lambda_{max}$, i=1, 2, . . . , n,
$Unif(\lambda_j)$ is the uniformity of the brightness level of the sample 106 for a single range or multiple ranges of wavelengths where $\lambda_{min} < \lambda_j < \lambda_{max}$, i=1, 2, . . . , n,
n is the number of spatial points for the image in horizontal direction,
m is the number of spatial points for the image in vertical diretion, and $i_{xy}$ is the combined incident radiation and fluorescence emissions level of the sample 106 at coorindate location of x and y at wavelength $\lambda_j$.

We also define the term fluorescence graph, which presents the emitted fluorescence level of the sample 106 to different radiation 122 parameters and the incident. The intent of the fluorescent graph is to enable an easier and better characterization of the fluorescence of the sample 106. This also may be beneficial during the formulation of the fluorescent pigments process.

As stated earlier, the radiation subsystem 114 can be controlled by processor 136 for different radiation 122 levels and spectral characteristics. Furthermore, the sensing subsystem 126 can also be controlled by processor 136 for spectral sensing of the emitted fluorescence signal 124.

Figure 3A:
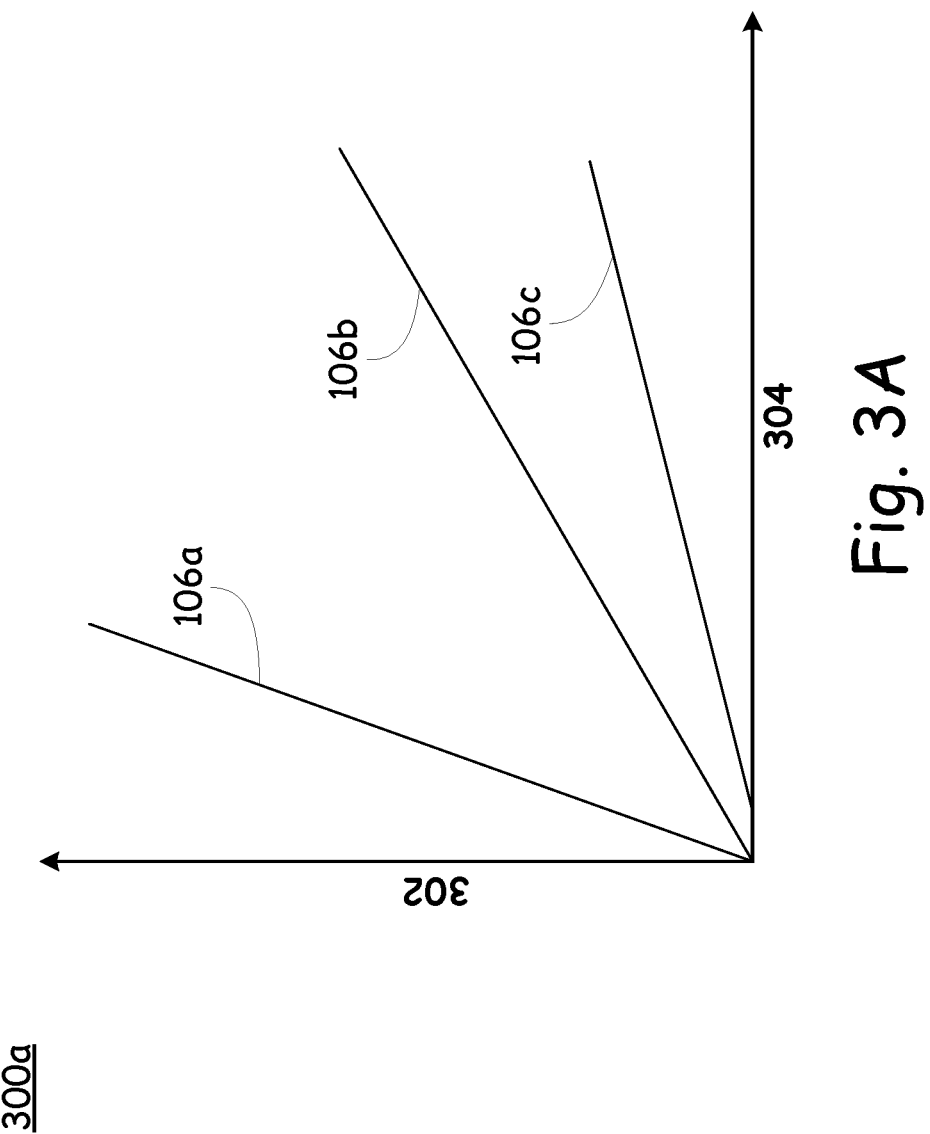
FIG. 3A is a fluorescence graph of radiation level versus fluorescence level for three different materials, according to an embodiment of the present invention.
Figure 3B:
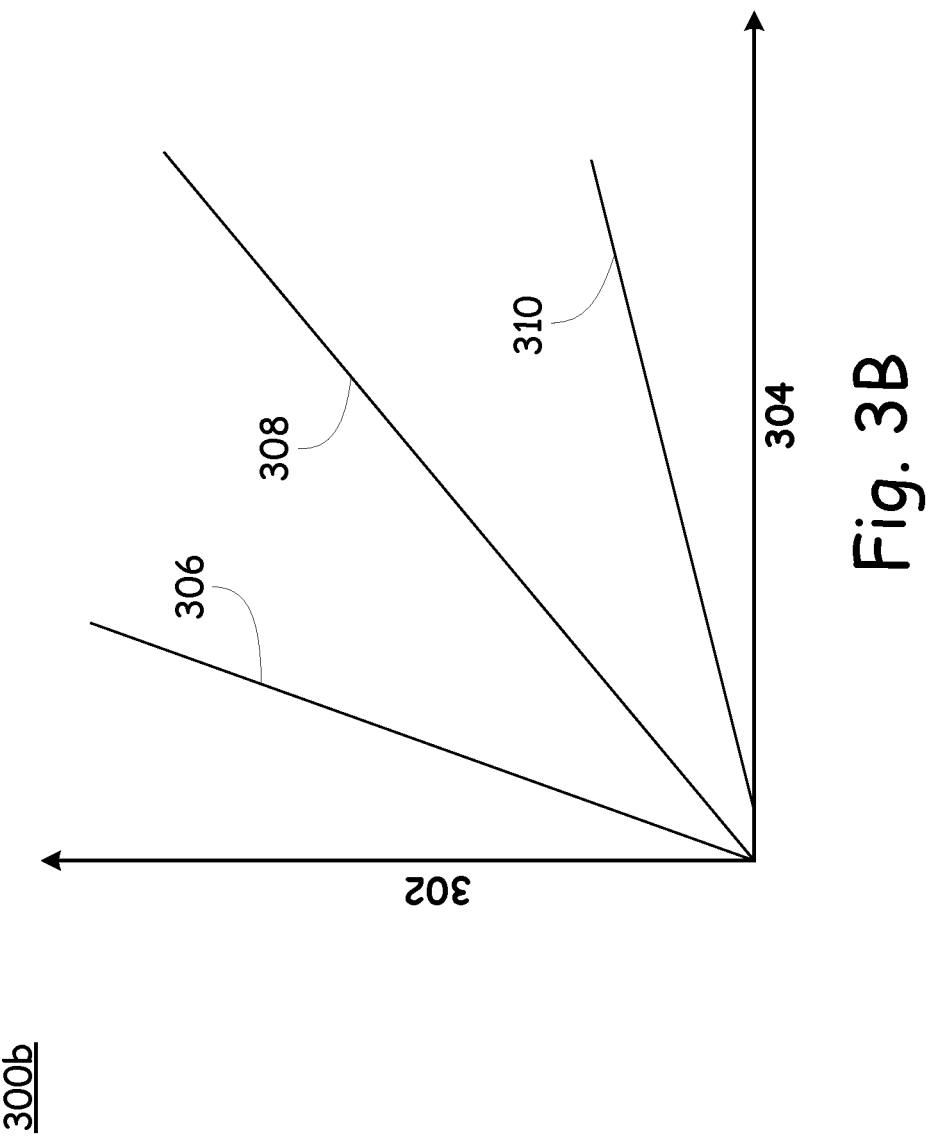
FIG. 3B is a fluorescence graph of radiation level versus fluorescence level for three different radiation wavelengths, according to an embodiment of the present invention.
Figure 3C:
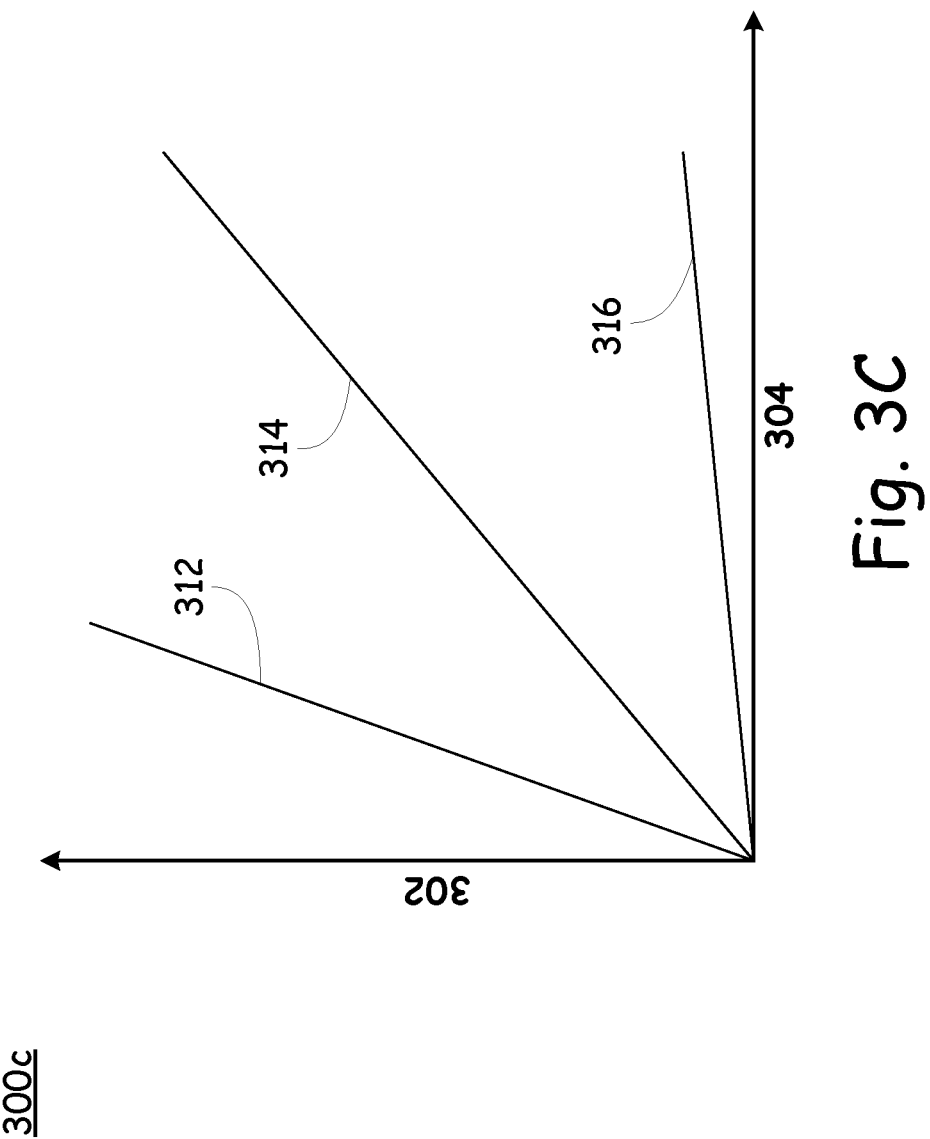
FIG. 3C is a fluorescence graph of radiation level versus fluorescence level for three different fluorescence wavelengths, according to an embodiment of the present invention.

FIGS. 3A-3C depict an example of how various samples 106a-106c react to various radiation 122 levels. This characterization quantifies the optimum radiation 122 level for a given fluorescent application requirement.

FIG. 3A depicts an example 300a where three different samples 106a-106c of fluorescent pigments are exposed to varying levels of radiation 122, and graphed as the fluorescence level of each sample 106a-106c on the y-axis 302, versus the radiation 122 level on the x-axis 304. This enables quantitative comparison and selection of the optimum samples of fluorescent pigments for a given application.

FIG. 3B shows an example 300b where one sample 106 of a fluorescent pigment is exposed to three different radiations 306, 308, and 310 with different spectral characteristics. FIG. 3C shows an example 300c where one sample 106 of a fluorescent pigment is exposed to one radiation with different spectral characteristics, and produces fluorescence at three wavelengths 312, 314, and 316. Based on the application, these graphs can help with understanding and selecting an optimum radiation source and emission outputs.

Pattern Analysis

The second measurement category is based on pattern analysis, which provides pattern information once it is found. The main difference between statistical analysis and pattern analysis is the inclusion of spatial information. In pattern analysis, the location and relationship among all pixels in an image are considered, whereas in statistical analysis, the spatial information is not considered.

Pattern analysis may include (a) the number of patterns found in the fluorescent image, (b) the total area of all patterns in the fluorescent image, (c) the average size of all patterns, (d) the percentage of patterns with a horizontal orientation, (e) the percentage of patterns with a vertical orientation, and (f) the percentage of patterns with a non-ordinal, or random, orientation.

We define the pattern set:

$$P(\lambda_j) = \{p_1, p_2, \ldots, p_l\}, \quad (6)$$

where $P(\lambda_j)$ is a set of fluorescent patterns $p_1$ through $p_l$ that are present in the fluorescent image $FI(\lambda_j)$ for a single range or multiple ranges of wavelengths where $\lambda_{min} < \lambda_j < \lambda_{max}$, 1, 2, . . . , k.

Each pattern $p_l$ contains a group of pixels $i_{xy}$ in a cluster with a clustering requirement. Clustering requirements can vary from application to application. One example is when all adjacent $i_{xy}$ having values larger than either a static or dynamically computed threshold.

Examples of fluorescent patterns 402, 404, and 406 are shown in pattern diagram 400 of FIG. 4. In this example, there are three fluorescent patterns 402, 404, and 406, where each pattern 402, 404, and 406 has a different orientation and size as shown. For example, pattern 402 is a substantially horizontal pattern, while pattern 404 is a substantially vertical pattern. Pattern 406 is a non-ordinal or random pattern.

In addition to categorizing the orientation of the patterns 402, 404, and 406, the size of each pattern 402, 404, and 406 is also computed. In the example 400 as depicted, pattern 402 is approximately 5.2% of the total field of view, pattern 404 is approximately 2.1% of the total field of view, and pattern 406 is approximately 11.2% of the total field of view.

Thus, various embodiments of the apparatus and method as described herein provide a more thorough analysis of the fluorescence of textiles, by providing fluorescence data at highly selectable radiation 122 profiles, and providing fluorescence data in a two-dimensional image of the sample 106, along with other benefits as described herein.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An apparatus (100) for measuring reflected radiation and fluorescence of a textile sample (106), the apparatus (100) comprising:
  a presentation subsystem (102) comprising a viewing window (108),
  a radiation subsystem (114) comprising a tunable radiation source (120) adapted to direct a desired radiation (122) having a wavelength range and an intensity through the viewing window (108) toward the sample (106), and causing the sample (106) to produce a fluorescence (124),
  a sensing subsystem (126) comprising an imager (130) adapted to capture the reflected radiation and fluorescence (124) in an array of pixels (408), where each pixel (408) records an intensity of the fluorescence (124) at the pixel location, and
  a control subsystem (132) comprising a processor (136) adapted to control the presentation subsystem (102), the radiation subsystem (114), and the sensing subsystem (126), and to create a reflected radiation and fluorescence image (400) containing both spectral information and spatial information in regard to the reflected radiation and fluorescence (124) of the sample (106),
  where the control subsystem (132) is configured to perform a pattern analysis with the reflected radiation and fluorescence image (400), which pattern analysis includes at least one of,
    (a) a number of patterns found in the brightness image,
    (b) a total area of all patterns in the brightness image,
    (c) an average size of all patterns,
    (d) a percentage of patterns with a horizontal orientation,
    (e) a percentage of patterns with a vertical orientation, or
    (f) a percentage of patterns with a nonordinal orientation.

2. The apparatus of claim 1, wherein the presentation subsystem (102) further comprises a sample press (104) adapted to press the sample (106) against the viewing window (108).

3. The apparatus of claim 1, wherein the presentation subsystem (102) further comprises calibration tiles (109) adapted to produce reflected radiation and fluorescence (124) with known characteristics in response to radiation (122) having known characteristics.

4. The apparatus of any claim 1, wherein the radiation subsystem (114) further comprises optics (118) adapted to shape and filter the radiation (122) from the tunable radiation source (120) before the radiation (122) achieves the sample (106).

5. The apparatus of claim 1, wherein the radiation subsystem (114) further comprises a detector (116) adapted to detect characteristics of the radiation (122).

6. The apparatus of claim 1, wherein the tunable radiation source (120) further comprises a source capable of producing two or more discrete radiation ranges.

7. The apparatus of claim 1, wherein the tunable radiation source (120) further comprises a radiation source capable of producing the radiation (122) at a desired intensity.

8. The apparatus of claim 1, wherein the radiation source (120) further comprises a source capable of producing two or more discrete radiation ranges, and further capable of independently producing each of the two or more radiation ranges at different desired intensities.

9. The apparatus of claim 1, wherein the sensing subsystem (126) further comprises an imager (130) adapted to capture the reflected radiation and fluorescence (124) in a two-dimensional array of pixels (408).

10. The apparatus of claim 1, wherein the sensing subsystem (126) further comprises a variable filter (128) adapted to selectively prohibit portions of the fluorescence (124) from achieving the imager (130).

11. The apparatus of claim 1, wherein the control subsystem (126) further comprises a machine interface (134) adapted to receive commands from and send information to another instrument.

12. The apparatus of claim 1, wherein the control subsystem (132) further comprises a human interface (138) adapted to receive commands from and send information to a user.

13. The apparatus of claim 1, wherein the control subsystem (132) is configured to classify patterns (402, 404, 406) in the reflected radiation and fluorescence image (400), including a percentage of the reflected radiation and fluorescence image (400) individually represented by each one of the patterns (402, 404, 406).

14. The apparatus of claim 1, wherein the control subsystem (132) is configured to classify patterns (402, 404, 406) in the reflected radiation and fluorescence image (400), including an orientation of each one of the patterns (402, 404, 406), where the orientation is at least one of horizontal, vertical, and non-ordinal.

15. A method for measuring fluorescence (124) of a textile sample (106), the method comprising the steps of:
  presenting the sample (106) against a viewing window (108) with a presentation subsystem (102),
  directing a desired radiation (122) having a wavelength range and an intensity from a radiation source (120) through the viewing window (108) toward the sample (106), thereby causing the sample (106) to produce a fluorescence (124),
  capturing the reflected radiation and fluorescence (124) with a sensing subsystem (126) including an imager (130) in an array of pixels (408), where each pixel (408) records an intensity of the reflected radiation and fluorescence (124) at the pixel location, and with a processor (136), controlling the presentation subsystem (102), the radiation subsystem (114), and the sensing subsystem (126), and creating a reflected radiation and fluorescence image (400) containing both spectral information and spatial information in regard to the reflected radiation and fluorescence (124) of the sample (106), where the processor (136), performs a pattern analysis with the fluorescent and reflected radiation image (400), which pattern analysis includes at least one of,
(a) a number of patterns found in the brightness image,
(b) a total area of all patterns in the brightness image,
(c) a average size of all patterns,
(d) a percentage of patterns with a horizontal orientation,
(e) a percentage of patterns with a vertical orientation, or
(f) a percentage of patterns with a nonordinal orientation.

16. The method of claim 15, further comprising pressing the sample (106) against the viewing window (108) with a press (104).

17. The method of claim 15, further comprising shaping and filtering the radiation (122) from the radiation source (120) with optics (118) before the radiation (122) achieves the sample (106).

18. The method of claim 15, further comprising detecting characteristics of the radiation (122) with a detector (116).

19. The method of claim 15, further comprising producing two or more discrete radiation ranges at desired intensities.

20. The method of claim 15, further comprising selectively prohibiting portions of the reflected radiation and fluorescence (124) from achieving the imager (130).

21. The method of claim 15, further comprising classifying patterns (402, 404, 406) in the reflected radiation and fluorescence image (400), including a percentage of the reflected radiation and fluorescence image (400) individually represented by each one of the patterns (402, 404, 406).

* * * * *